(12) United States Patent
Deladi et al.

(10) Patent No.: US 10,342,510 B2
(45) Date of Patent: Jul. 9, 2019

(54) INTERVENTIONAL DEVICE, METHOD OF ASSEMBLING, AND ASSEMBLING SYSTEM

(71) Applicant: KONINKLIJKE PHILIPS N.V., Eindhoven (NL)

(72) Inventors: Szabolcs Deladi, Veldhoven (NL); Cornelius Antonius Nicolaas Maria Van Der Vleuten, Liempde (NL); Antonius Johannes Josephus Rademakers, Eindhoven (NL); Johannes Gerardus Van Beek, Budel (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 757 days.

(21) Appl. No.: 14/440,622

(22) PCT Filed: Oct. 29, 2013

(86) PCT No.: PCT/IB2013/059743
§ 371 (c)(1),
(2) Date: May 5, 2015

(87) PCT Pub. No.: WO2014/072879
PCT Pub. Date: May 15, 2014

(65) Prior Publication Data
US 2015/0297178 A1 Oct. 22, 2015

Related U.S. Application Data

(60) Provisional application No. 61/723,825, filed on Nov. 8, 2012.

(51) Int. Cl.
*A61B 8/00* (2006.01)
*A61B 18/14* (2006.01)
(Continued)

(52) U.S. Cl.
CPC ............... *A61B 8/445* (2013.01); *A61B 8/12* (2013.01); *A61B 18/1492* (2013.01);
(Continued)

(58) Field of Classification Search
CPC ...................................................... A61N 7/022
See application file for complete search history.

(56) References Cited

U.S. PATENT DOCUMENTS

| | | | |
|---|---|---|---|
| 5,078,149 A | 1/1992 | Katsumata et al. |
| 5,688,266 A | 11/1997 | Edwards et al. |
| 6,064,905 A | 5/2000 | Webster et al. |
| 6,974,422 B1 | 12/2005 | Millar |

(Continued)

FOREIGN PATENT DOCUMENTS

| | | |
|---|---|---|
| CN | 2574631 Y | 9/2003 |
| JP | 1277540 A | 11/1989 |

(Continued)

*Primary Examiner* — Luther Behringer (57) ABSTRACT

The invention relates to an interventional device (10) including a plurality of signal assemblies, a method of assembling such interventional device (10), an assembling system for such interventional device (10) and a corresponding software product. In order to provide a number of signal assemblies including, for example, ultrasound transducers (40) in an interventional device (10) with a reduced risk of thrombi formation or similar complications a desired flush and smooth surface of a casing (15) of the interventional device (10) is achieved if the signal assemblies are inserted in such a manner that they are urged into their respective positions from inside the casing (15) after such insertion.

7 Claims, 7 Drawing Sheets

(51) Int. Cl.
*A61B 8/12* (2006.01)
*A61N 7/02* (2006.01)
*A61B 17/00* (2006.01)
*A61B 18/00* (2006.01)
*A61N 7/00* (2006.01)
*A61B 90/00* (2016.01)

(52) U.S. Cl.
CPC .... *A61N 7/022* (2013.01); *A61B 2017/00106* (2013.01); *A61B 2017/00526* (2013.01); *A61B 2018/0088* (2013.01); *A61B 2018/00351* (2013.01); *A61B 2018/00577* (2013.01); *A61B 2018/00821* (2013.01); *A61B 2018/00839* (2013.01); *A61B 2018/00994* (2013.01); *A61B 2090/3784* (2016.02); *A61B 2562/12* (2013.01); *A61N 2007/0052* (2013.01)

(56) References Cited

U.S. PATENT DOCUMENTS

| | | |
|---|---|---|
| 6,979,329 B2 | 12/2005 | Burnside et al. |
| 8,214,010 B2 | 7/2012 | Courtney et al. |
| 9,737,323 B2 | 8/2017 | Thaplyal et al. |
| 9,949,791 B2 | 4/2018 | Clark et al. |
| 2008/0243214 A1 | 10/2008 | Koblish |
| 2009/0163916 A1 | 6/2009 | Paul et al. |
| 2010/0331658 A1 | 12/2010 | Kim et al. |
| 2013/0060245 A1 | 3/2013 | Grunewald et al. |
| 2013/0172742 A1 | 7/2013 | Rankin et al. |
| 2014/0148703 A1 | 5/2014 | Deladi et al. |

FOREIGN PATENT DOCUMENTS

| | | | |
|---|---|---|---|
| JP | 2001238885 A | 9/2001 | |
| JP | 2008284136 A | 11/2008 | |
| WO | WO2012066430 | * 5/2012 | ........... A61B 8/4483 |

* cited by examiner

INTERVENTIONAL DEVICE, METHOD OF ASSEMBLING, AND ASSEMBLING SYSTEM

CROSS-REFERENCE TO PRIOR APPLICATIONS

This application is the U.S. National Phase application under 35 U.S.C. § 371 of International Application Serial No. PCT/IB2013/059743, filed on Oct. 29, 2013, which claims the benefit of U.S. Application Ser. No. 61/723,825, filed on Nov. 8, 2012. These applications are hereby incorporated by reference herein.

FIELD OF THE INVENTION

The invention relates to an interventional device including a plurality of signal assemblies, a method of assembling such interventional device, an assembling system for such interventional device and a corresponding software product.

BACKGROUND OF THE INVENTION

An example for the use of an interventional device is cardiac ablation which is a procedure for curing cardiac arrhythmia. Preferably, the process of the cardiac ablation is monitored in situ. An ablation catheter with multiple ultrasound transducers in its tip enables the physician in the electro-physiology lab to assess in real time certain relevant parameters of the heart wall from the inside.

An example of an ultrasound transducer system for cardiac ablation monitoring in discussed in WO 2012/066430 A1.

However, unless a casing transparent to the monitored signal (e.g. ultrasound) is employed, i.e. if there are openings in the casing of the interventional device through which signals are emitted or received, complications during the treatment procedure may be caused by discontinuities in the surface of the interventional device.

In particular, if there is a mechanical discontinuity on the ablation catheter tip, there is a potential of thrombi formation, which can cause thromboembolic events with severe consequences (e.g. a stroke).

Openings which are provided in the case for irrigation purposes, for example, usually do not pose such threat as there is a (continuous) flow of saline irrigation fluid during the procedure. In contrast, in the case of an opening of the casing which might even include a distinct step between a surface of the transducer arrangement and the outer surface of the casing, such step is a potential site for thrombi formation due to the lack of a forced flow in such regions during treatment procedure.

SUMMARY OF THE INVENTION

It is an object of the present invention to provide an interventional device with a reduced risk of thrombi formation or similar complications, together with a method of assembling such interventional device, an assembling system for such interventional device and a corresponding software product.

In a first aspect of the present invention an interventional device is presented, comprising a casing with a side wall having a plurality of openings extending in a directions oblique to a longitudinal axis of the casing, and a plurality of signal assemblies, each including a sensor and/or an emitter, each signal assembly being aligned with a respective opening of the casing for receiving and/or emitting signals through the opening, wherein each signal assembly of the plurality of signal assemblies extends from the inside of the casing into the respective opening such that an outer surface of the signal assembly and an outer surface of the casing are flush at an edge of the opening and the outer surface of the signal assembly and the outer surface of the casing form a smooth outer surface of the interventional device, wherein the signal assemblies are fixed in the respective openings from inside the casing by a fixing element.

In a further aspect of the present invention a method of assembling an interventional device is presented, comprising the steps of providing a casing with a side wall having a plurality of openings extending in a directions oblique to a longitudinal axis of the casing, inserting a plurality of signal assemblies into the casing, each signal assembly including a sensor for receiving and/or an emitter for emitting signals through an opening of the casing, and aligning each signal assembly of the plurality of signal assemblies with a respective opening of the casing, and urging the signal assemblies into the respective openings such that outer surfaces of the signal assemblies and an outer surface of the casing are flush at edges of the openings and the outer surfaces of the signal assemblies and the outer surface of the casing form a smooth outer surface of the interventional device, wherein the urging is provided by inserting a fixing element into the casing, the inserted fixing element fixing the signal assemblies in the respective openings from inside the casing.

In yet a further aspect of the present invention assembling system for an interventional device is presented, comprising a holder for a casing with a side wall having a plurality of openings extending in directions oblique to a longitudinal axis of the casing, a first inserter for a plurality of signal assemblies, each signal assembly including a sensor for receiving and/or an emitter for emitting signals through respective opening of the casing, and a second inserter for a fixing element, the fixing element being provided for fixing the signal assemblies in the casing, wherein the second inserter is arranged for urging the signal assemblies of the plurality of signal assemblies, each signal assembly being aligned with the respective opening of the casing, into the respective openings such that outer surfaces of the signal assemblies and an outer surface of the casing are flush at edges of the openings and the outer surfaces of the signal assemblies and the outer surface of the casing form a smooth outer surface of the interventional device, the urging being provided by inserting the fixing element into the casing.

It was realized by the inventors that—in order to provide a number of signal assemblies like ultrasound transducers in an interventional device with a reduced risk of thrombi formation or similar complications—it would be necessary to provide the signal assemblies such that the outer surfaces of the signal assemblies and the outer surface of the casing are flush at edges of the openings and the outer surfaces of the signal assemblies and the outer surface of the casing form a smooth outer surface of the interventional device. In order to have such flush and smooth surfaces, however, it is necessary to at least partially place portions of the signal assemblies such that the outer surface of the casing is smoothly extended into the area of the openings. Even though with a rigid casing the insertion of a rigid structure of such signal assemblies is not possible, the flush and smooth surface may be achieved if the signal assemblies are inserted in such a manner that they are urged into their respective positions from inside the casing after such insertion.

It is to be noted that the term "smooth" does not exclude the case where a portion of a signal assembly projects beyond the general surface of the casing or is recessed from such general surface of the casing but it is be understood as an indication that the surface is multiple times differentiable (i.e. not necessarily continuously differentiable).

However, in view of a danger of tissue ruptures or current concentrations at protruding or recessing portions (possibly causing, for example, blood to be coagulated in the pool created by the mechanical discontinuity), generally an overall even and flat surface of the interventional device is preferred.

The definition that an opening extends in a direction oblique to the longitudinal axis of the casing means that a boring (i.e. the inner side walls of the opening) provides for a surface which is not parallel to the longitudinal axis. Accordingly, as a signal assembly in inserted into the opening such that a side surface of the signal assembly abuts the inner side walls of the openings, the direction of such insertion (and that of a force employed therefore) is inclined in relation to the longitudinal axis of the casing. In other words, an opening extending in an oblique direction in relation to the longitudinal axis would result from drilling through the wall of the casing with a drill having its axis not parallel to the longitudinal axis of the casing.

The oblique direction also includes the case that the direction is perpendicular to the longitudinal axis.

In a preferred embodiment, the signal assemblies are positively locked, respectively, between the casing and the fixing element and/or to the fixing element.

By virtue of a positive locking the signal assemblies are mechanically locked inside the casing, wherein therefore the fixing does not depend on a fixing like gluing (which is not excluded from being additionally provided) which might deteriorate under operation conditions. The positive lock of a signal assembly may be achieved by locking the signal assembly between the casing and the fixing element and/or by locking the signal assembly to or into the fixing element. It is to be noted that the locking may also be an indirect one, as for example, there might be a lining between the casing and the signal assembly. A locking of the signal assembly to or into the fixing element may be provided, for example, by a protrusion of the fixing element engaging into an undercut of the fixing element.

If the signal assemblies (and correspondingly other elements inside the casing) are locked inside the casing mechanically and not only by adhesive bonding or the like, a concern of losing parts due to failure of such bonding in view of stress caused by differential expanding/shrinking of materials in the context of thermal aspects (e.g., high frequency ablation) is addressed.

In a preferred embodiment, the interventional device further comprises one or more conduits defined by the casing, at least respective two of the signal assemblies and the fixing element.

By urging the signal assemblies into the respective openings of the casing, there might be provided an empty space between the signal assemblies, which is further enclosed by the inner wall surface of the casing and an outer surface of the fixing element. Such space then extends along a longitudinal axis of the interventional device forming a conduit between the casing, adjacent signal assemblies and the fixing element.

By means of an appropriate internal structure inside the interventional device two or more of such conduits may be brought into fluid connection, wherein then a fluid may flow into the interventional device in one conduit and flow out of the interventional device through another conduit.

In a modification of the above preferred embodiment of the interventional device, the casing further includes one or more through-holes in fluid connection to the one or more conduits.

If there is a fluid connection of a conduit as discussed above the outside (at the front end) of the interventional device, fluid may be delivered and/or removed through said through-holes. Thus, irrigation fluid (typically including saline) may be supplied to the tip or another portion of the interventional device; while alternatively or additionally body fluids (e.g. blood) may be sampled from the areas surrounding the interventional device.

In addition and/or alternative to a through-hole other means for exchange or transfer of fluids and/or components of fluids may be used, e.g. a semi-permeable membrane.

Alternatively or additionally to the above provision of conduits due to the positioning of the signal assemblies, the signal assemblies as such and/or the fixing element (as well as the casing as such) may include conduits formed therein, which might be used in a corresponding manner.

In a preferred embodiment of the interventional device, a signal assembly includes a signal interface at least partially covering the sensor and/or emitter such that the outer surface of the signal assembly is at least partially a surface of the signal interface.

Depending on the circumstances of the signal emission or reception it might be advantageous to provide an interface between the sensor/emitter and the surrounding area to be monitored or to be provided with a signal.

In consideration of the reverberation caused by the excitation pulse of an ultrasound transducer, for example, it is preferable that the transducer is placed at a distance from the surface to be imaged (e.g. in case of imaging thin tissue of 0.5 to 2-4 mm).

If a transducer is excited, an echo resulting from tissue close by is very difficult if not impossible to detect as such echo arrives back at the transducer prior to a sufficient fading of the reverberations of the transducer caused by the excitation itself.

If however, there is provided a signal interface the ultrasound path to the region of the tissue at interest may be long enough for the reverberations to fade sufficiently.

Furthermore, if the interventional device has a curved circumference (e.g. is round in cross-section), for the outer surface of the casing and the outer surfaces of the signal assemblies being flush and forming a smooth outer surface of the interventional device, the outer surface of a signal assembly would typically also have to be curved. In most situations, it is easier and more cost effective to provide a signal interface having such curved outer surface on a conventionally flat signal emitter or receiver (sensor) than to provide a signal emitter or a sensor having such curved surface itself.

In a preferred embodiment of the interventional device, at least a part of said outer surface of a signal assembly is a surface of the sensor and/or emitter of the signal assembly.

Under circumstances differing from those discussed with respect to the previous embodiment, there might also be advantages involved with providing a surface of the sensor and/or emitter directly at the outer surface of the interventional device. If, for example, a sensor is provided for picking up electric or thermal signals, the present embodiment allows this without or at least with a reduced influence of additional material otherwise covering the sensor surface. A further case in which the sensor/emitter surface might coincide with the outer surface of the interventional device is one of optical fibers embedded in mechanical retention pieces, for which the end surfaces of the fiber are flush with the outer surface of the casing.

In a preferred embodiment of the interventional device, a signal assembly includes an adaptor provided between the sensor and/or emitter of the signal assembly and the fixing element.

It is preferable to provide a defined surface of the sensor assembly by providing an adaptor arranged between the sensor/emitter of the signal assembly and the fixing element in an assembled state of the interventional device. Similar to the above, most commercially available signal emitter or sensors (signal receiver) have a basically flat surface. In order to, for example, avoid the need for checking a particular orientation of the parts to be assembled, it is preferable to provide a configuration indifferent to the orientation: If the fixing element has a circular circumference in cross-section along the longitudinal axis of the interventional device and the adaptor comprises a corresponding concave shape, the fixing element may be inserted in any rotational state. Nevertheless, orientation indifference with a reduced degree is achievable by providing symmetry of rotation (e.g. a rectangular cross-section for indifference against a rotation by 180°, a triangular cross section for 120°, a square cross-section for 90°, etc.).

If, nevertheless, a particular orientation or rotational state of the fixing element in relation to the casing and/or the sensor assemblies is desirable, this might be achieved by providing, for example, one or more matching pairs of recess/protrusion for the related parts.

The signal assemblies, according to a further embodiment modifying the above, may be provided as having an integral element forming both, a signal interface and an adaptor, into which the sensor and/or emitter is included or inserted. In such case, the sensor interface and the adaptor might be of the same material (e.g. formed by injection molding). Nevertheless, suitable productions techniques (e.g. 2K-extrusion) may also allow for the use of different materials.

In a preferred embodiment of the interventional device, the casing further includes a front wall having a front opening, wherein the interventional device further includes a further signal assembly including an emitter for emitting and/or a sensor for receiving signals through the front opening, the further signal assembly extending from the inside of the casing into the front opening such that an outer surface of the further signal assembly and an outer surface of the front casing are flush at an edge of the front opening and the outer surface of the further signal assembly and the outer surface of the casing form a smooth outer surface of the interventional device.

In addition to obliquely directed signal assemblies (including a radial orientation), the interventional device may also have one or more sensors and/or emitters arranged such that the respective signal assembly may be inserted into the corresponding (front) opening of the casing in a direction along the longitudinal axis of the interventional device.

It is to be noted that this arrangement also applies to a case in which a signal assembly is directed in an oblique direction with respect to the longitudinal axis of the interventional device if the corresponding opening is provided that the signal assembly may be inserted therein just or basically by movement along the longitudinal axis of the casing, i.e. if the boring of the opening provides for a surface parallel to the longitudinal axis.

The casing, the fixing element and/or the portion of the signal assembly preferably allow for an efficient cooling of the sensors/signal emitters, which is advantageous in particular in case of a continuous operation or in case of other reasons for production of heat, especially in the context of (cardiac or other) ablation.

Aside from such considerations, however, the choices for the materials of the parts involved in the interventional device according to the present invention are generally only limited by their respective purposes and the constraints given for their operation. Generally, metallic material, ceramics, plastics and combinations thereof are suitable materials.

In a preferred embodiment of the method of assembling, the fixing element is provided with a chamfer on its distal end and/or is tapering at its distal end, wherein the signal assemblies are guided by the chamfer and/or tapering to an outer surface of the fixing element upon inserting the fixing element.

A fixing element provided with a chamfered or tapered front end allows for an easy insertion, in particular as there is a self-centering effect involved.

In a preferred embodiment of the method of assembling, the inserting of the fixing element includes a turning of the fixing element inside the casing.

In addition to the above or alternatively the fixing element may include protrusions or projections which urge the signal assemblies (which might be provided with corresponding elements) into the openings upon turning or rotating the fixing element (either in its completely inserted position or at an earlier stage of the insertion).

In a preferred embodiment of the method of assembling, the inserting of the fixing element includes a deforming of the fixing element inside the casing.

If, for example, the fixing element is loaded with a pressure along the longitudinal axis of the casing/interventional device (i.e. along the direction of insertion) and the fixing element reacts to such pressure by deformation, the deforming of the fixing element may be used for urging the signal assemblies into their respective openings.

In a modification of the above preferred embodiment of the method of assembling, the fixing element is inserted in compacted form and the deforming of the fixing element includes an expansion.

Prior to inserting into the case, the fixing element and the signal assemblies may be provided together, wherein a radially acting pressure is applied such that the fixing element (basically surrounded by the signal assemblies) is compacted. The pressure/compaction is maintained and the fixing element is inserted into the casing together with the signal assemblies and the fixing element is allowed to relax (i.e. to expand) inside the case, thus urging the signal assemblies into their designated positions. Alternatively, the signal assemblies may be provided inside the casing already, wherein the compacted fixing element is inserted (e.g. kept compacted by means of a shell), followed by an expansion (e.g. due to removal of the shell) inside the casing.

In a preferred embodiment of the method of assembling, at least one of the signal assemblies is inserted into the casing such that a deformable surface of said signal assembly is aligned with the respective opening of the casing, wherein the inserting of the fixing element causes, upon urging said signal assembly, a deforming of the deformable surface.

In case of a substantially rigid (surface of the) signal assembly, the signal assembly includes a protrusion or swell which, in the assembled state, extends into the respective opening. If the (surface of the) signal assembly is deformable (e.g. elastic or otherwise compressible), however, the signal assembly in its undeformed state may have no such protrusion or swell or a smaller one in comparison to the above case, wherein the extending of the signal assembly into the respective opening (i.e. the flush outer surface of the interventional device) is provided by inserting the fixing element, which deforms (e.g. compresses) the signal assembly, Accordingly, a substantially or at least mostly undeformed portion of the signal assembly extends into the opening and a deformed portion of the signal assembly abut (directly or indirectly) the inner surface of the casing and is compressed between the casing and the fixing element.

In a further aspect of the present invention a software product for assembling an interventional device is presented, the software product comprising program code means for causing the assembling system according to the present invention to carry out the steps of the method according to the present invention when the software product is run on the assembling system.

It shall be understood that the interventional device, the method of assembling an interventional device, and the assembling system as disclosed herein have similar and/or identical preferred embodiments, in particular, as defined in the claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
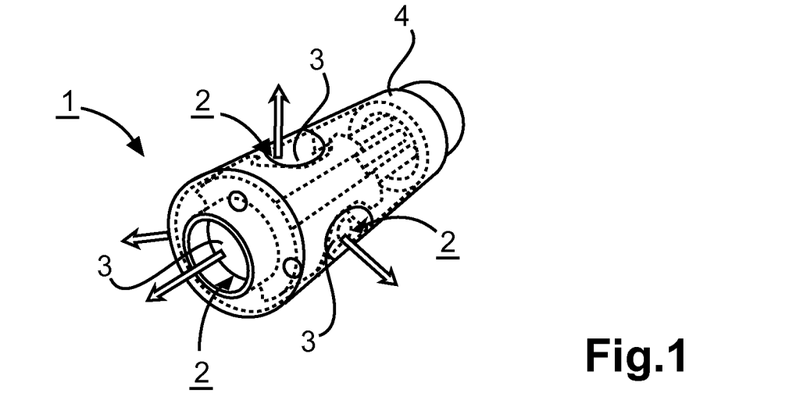
FIG. 1 shows an ablation catheter tip with integrated sensors.

FIG. 1 shows an ablation catheter tip 1, which includes one front transducer 3 and three further transducers 3 directed sidewise, which are provided inside a casing 4 of the ablation catheter tip. The casing 4 comprises openings 2, through which the transducers 3 transmit and receive ultrasound signals. The transducers 3 do not extend into the openings 2 and accordingly the surface of the ablation catheter tip 1 includes recesses at the position of the openings 2.

Figure 2A:
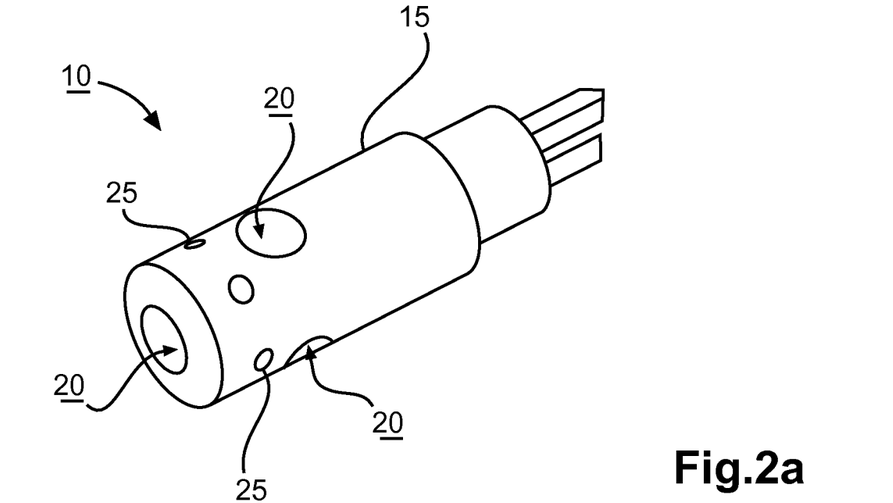
FIG. 2a and 2b show different views of an ablation catheter tip in accordance with an embodiment of the invention.
Figure 2B:
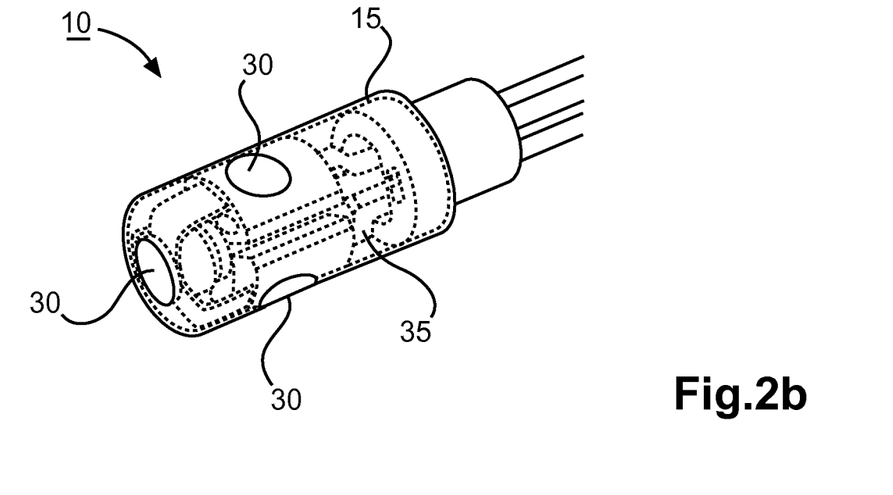

FIG. 2a shows a first view of an ablation catheter tip as an example of an interventional device in accordance with an embodiment of the invention. The ablation catheter tip 10 includes a casing 15 having plural openings 20 and several through-holes 25. FIG. 2b shows another view of the ablation catheter tip 10 of FIG. 2a, where the casing 15 is shown as being transparent for illustrative reasons. Inside the casing 15, signal interfaces 30 of the signal assemblies of the ablation catheter tip can is shown together with wiring 35 of the signal assemblies. The signal interfaces 30 extend into the openings 20 of the casing 15 such that the outer surfaces of the signal interfaces 30 are flush with the outer surface of the casing 15 and the combined surface of the casing 15 and the signal interfaces 30 is smooth.

Figure 3A:
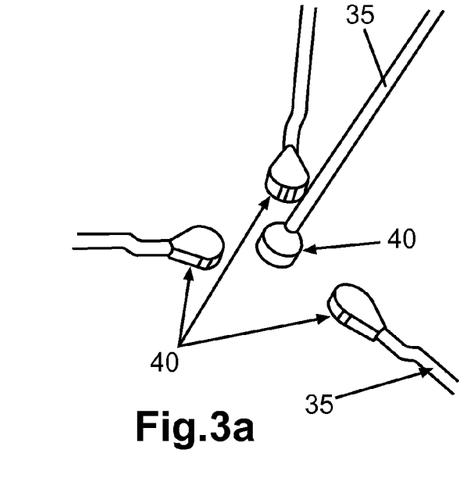
FIG. 3a to 3e show elements of an ablation catheter tip in accordance with the embodiment of FIG. 2a and 2b, FIG. 4a to 4k illustrate an assembling of the ablation catheter tip using the elements shown in FIG. 3a to 3e, FIG. 5a to 5c show sectional views of an ablation catheter tip in accordance with another embodiment of the invention.

FIG. 3a shows transducers 40 of an ablation catheter tip in accordance with the embodiment of FIG. 2a and FIG. 2b in unassembled state together with their respective wiring 35.

Figure 3B:
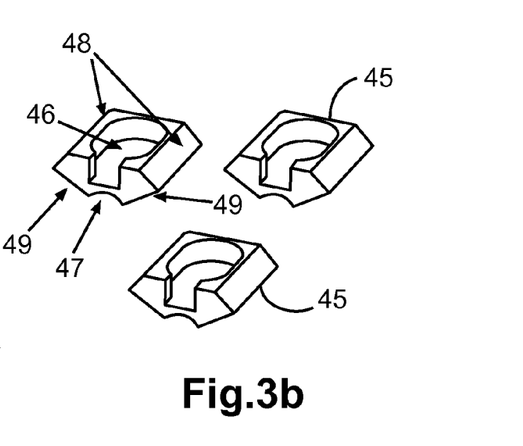

FIG. 3b shows adaptors 45 of an ablation catheter tip in accordance with the embodiment of FIG. 2a and FIG. 2b. The adaptors 45 each comprise a seat 46 provided to receive the transducers 40. Further, the adaptors each include an inner seat surface 47, which in assembled state will be in contact with the fixing element (see FIG. 3d). The adaptors further have outer seat surfaces 48 which will be in contact, in assembled state, with an inner surface of the casing 15 (see FIG. 3e). Further, the adaptors 45 are provided with contact surfaces 49, which are in abutment with corresponding contact surfaces 49 of adjacent adaptors in a state of the assembling prior to the insertion of the signal assembly into the casing (see FIG. 4g).

Figure 3C:
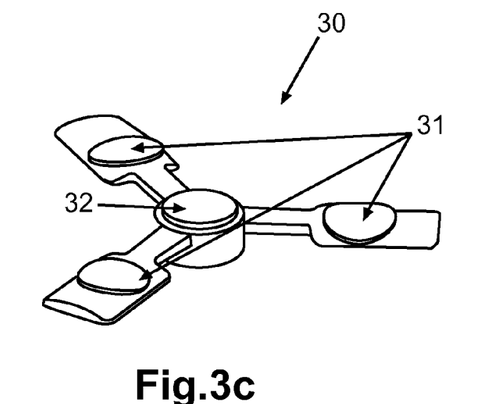

FIG. 3c shows a signal interface 30 of an ablation catheter tip in accordance with the embodiment of FIG. 2a and 2b. The signal interface 30 includes projections for radial interfaces 31 and a projection for an axial interface 32, wherein these projections, in assembled state, extend into the openings of the casing in order to achieve a flush outer surface.

Figure 3D:
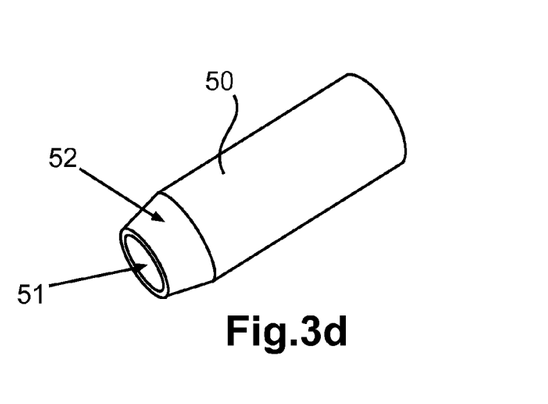

FIG. 3d shows a fixing element 50 of an ablation catheter tip in accordance with the embodiment of FIG. 2a and 2b. The fixing element 50 is provided as a hollow tube having a nozzle 51 therein, through which the wiring 35 of the front transducer is provided. The front portion of the fixing element 50 is provided with a chamfer 52 for easing the insertion of the fixing element between the adaptors 45 upon inserting the fixing element 50 into the casing 15.

Figure 3E:
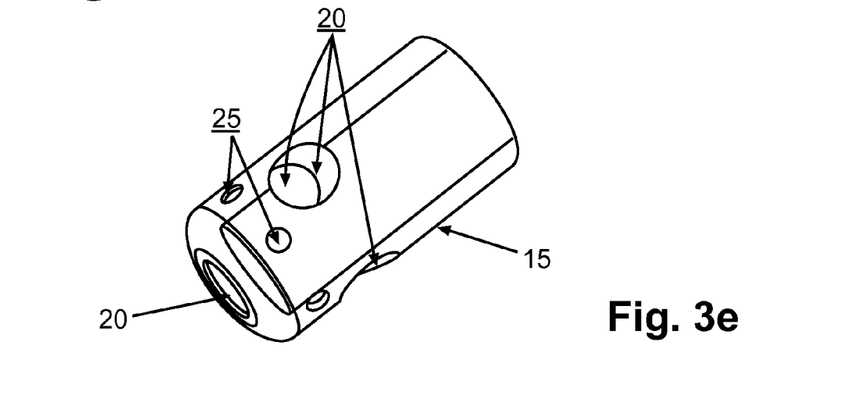

FIG. 3e shows a casing 15 of an ablation catheter tip in accordance with the embodiment of FIG. 2a and FIG. 2b. The casing 15 is provided with (i) an opening 20 at the front end of the casing and (ii) openings 20 at the side wall of the casing 15. Further, the casing 15 is provided with through-holes 25 provided in an area between the front opening 20 and the side wall openings 20.

Figure 4A:
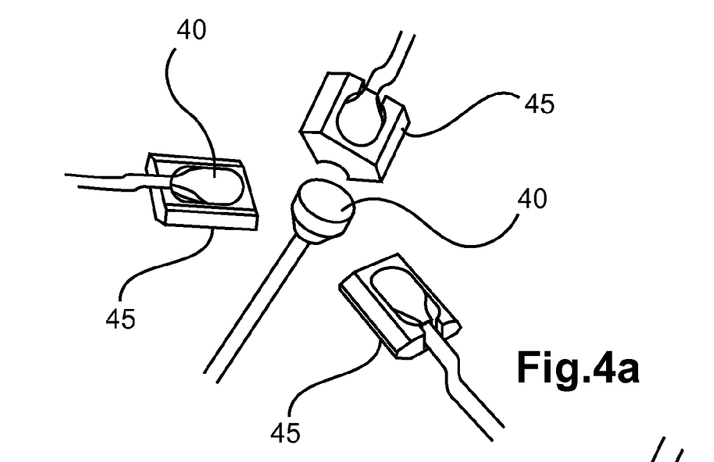
Figure 4B:
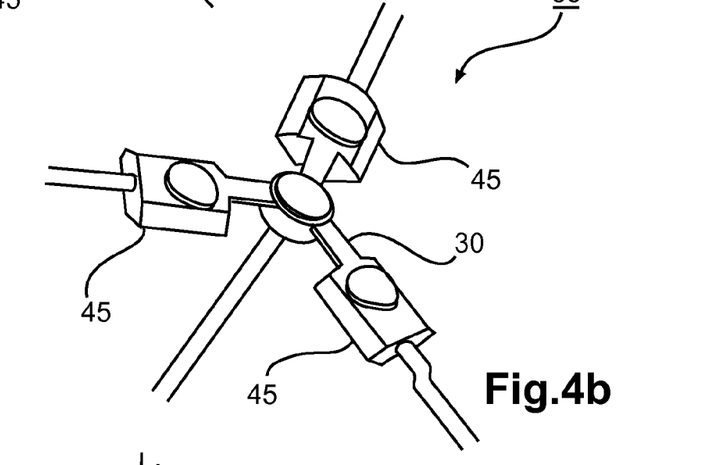

FIG. 4a illustrates a first step of an assembling of the ablation catheter tip using the elements shown in FIG. 3a and 3b. The transducers 40 intended for the side openings of the casing are provided with their respective adaptors 45. For the front transducer there is no adaptor provided. FIG. 4b illustrates a further step of the assembling of the ablation catheter tip using the elements shown in FIG. 4a and FIG. 3c. The signal interface 30 is provided on the transducers 40 shown in FIG. 4a combined with their respective adaptors 45.

Figure 4C:
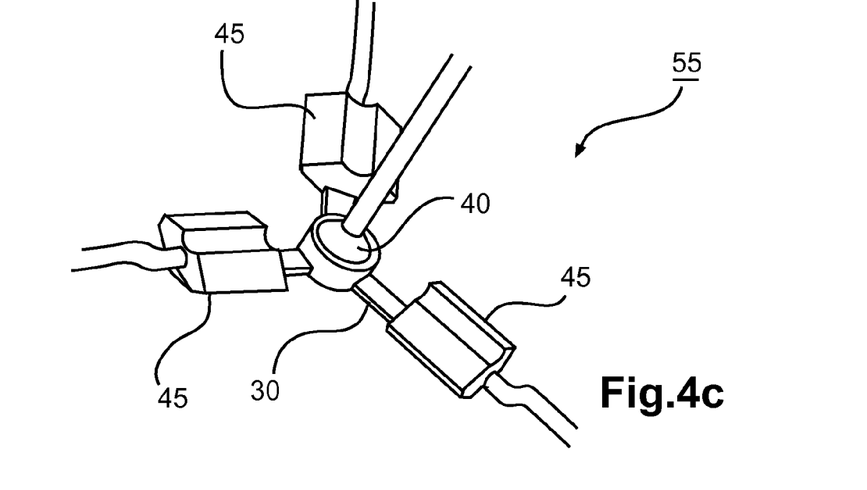

FIG. 4c shows a different view of the assembling state illustrated in FIG. 4b.

FIG. 4b and FIG. 4c show a sub-assembly 55 including the plurality of signal assemblies including the transducers 40, their adaptors 45 and the signal interfaces 30.

It is to be noted that the order of assembly indicated in FIG. 4a to 4c may also be changed depending on the circumstances, e.g. it is also possible to attach the transducers 40 first to the signal interface 30 (or vice versa) and to add thereafter the adaptors 45 to complete the sub-assembly 55. It is further possible to provide a mixture of these approaches, e.g. to attach some of the adaptors 45 to the transducers 40 (or vice versa), followed by attaching (some of) the signal interfaces 30, followed by attaching further adaptors 45, etc.

The signal interfaces do not necessarily have to be connected to each other, even though such connections by runners or the like provides an advantage in basically fixing the spatial relation between the transducers (signal emitters/sensors) (while maintaining a possibility of flexing the runners), facilitating any easy handling of the sub-assembly 55.

In this embodiment, the radial transducers 40 are glued to the adaptors 45 (using an epoxy resin adhesive, e.g., ARALDITE™) and also to the signal interface 30 (made of polyether block amide, e.g., PEBAX™). If, as in this case, the material of the signal interface is transparent, UV curing may be used for binding the pieces together.

Figure 4D:
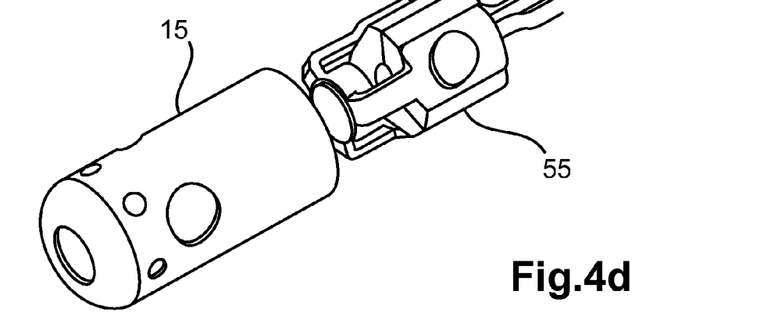
Figure 4E:
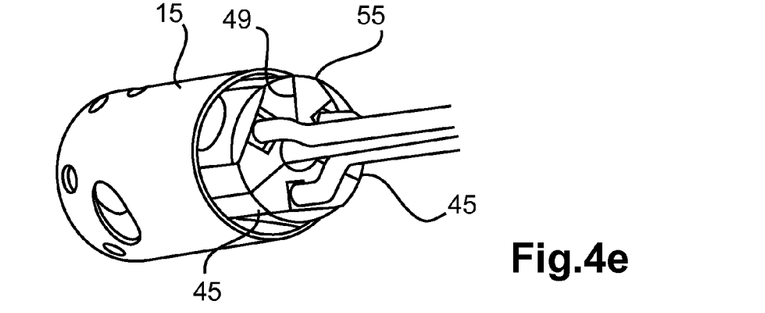

FIG. 4d shows a further step of the assembling of the ablation catheter tip using the elements shown in FIGS. 4b, 4c and 4e. The sub-assembly 55 shown in FIG. 4b and FIG. 4c is folded such that the adaptors 45 of the transducers provided for the side openings of the casing are almost in abutment with the wiring of the front transducer 40, wherein the total cross section of the sub-assembly 55 is narrow enough to be inserted into the casing 15.

Figure 4F:
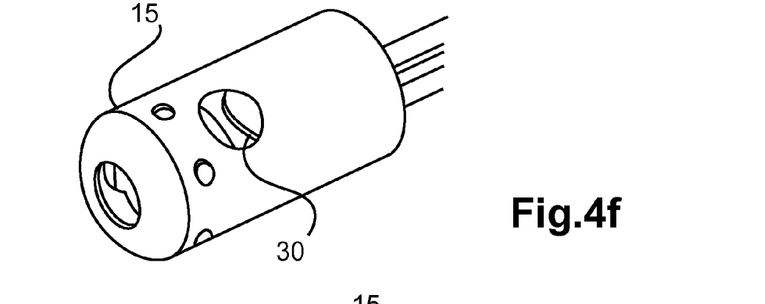

FIG. 4e and 4f illustrate a further state of the assembling of the ablation catheter tip resulting from a partial insertion of the sub-assembly shown in FIG. 4d into the casing 15. As it can been seen in FIG. 4e, the contact surfaces 49 of the adaptors 45 are in contact with each other such that the total cross-section of the sub-assembly 55 is small enough to fit into the casing 15.

Figure 4G:
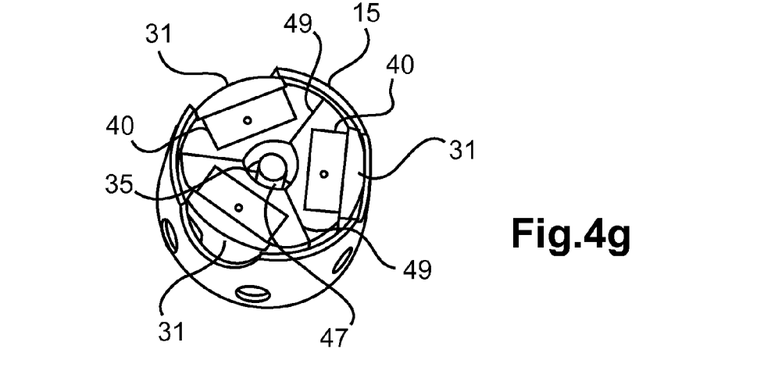

FIG. 4g shows a cross-sectional view of the state of the assembly shown in FIG. 4e and FIG. 4f. The adaptors 45, the contact surfaces 49 of which are in contact with each other are arranged around the wiring 35 of the front transducer (not shown), while the transducers 40 are provided in the adaptors. The transducers 40 are covered, respectively, by the signal interfaces 31 which are to be provided eventually into the openings of the casing 15. Between the wiring 35 and the inner surface 47 of the adaptors 45 there is space for an initial insertion of the fixing element.

Figure 4H:
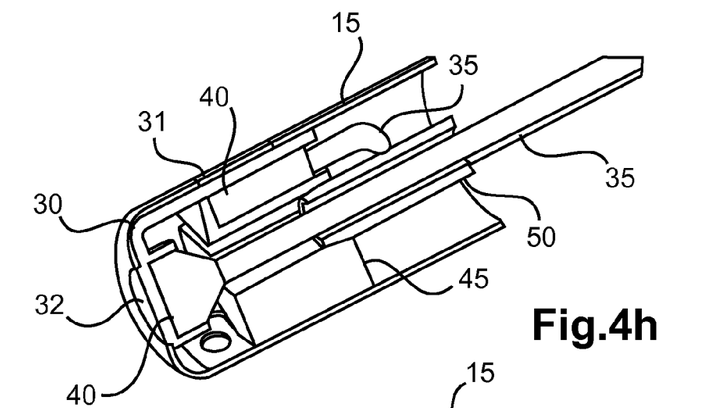

FIG. 4h shows a further state in the assembling of the ablation catheter tip following the state shown in FIGS. 4e to 4g. The transducers 40 inside the signal assemblies including the signal interface 30 and the adaptors 45 are basically provided in alignment with the openings of the casing 15. The front transducer 40 with the respective axial interface 32 is aligned with an opening on the front of the casing, while the other transducers 40 are provided with the radial interfaces 31 (only one shown) at the openings in the side wall of the casing 15. Along the wiring 35 of the front transducer 40, the fixing element 50 is provided and inserted between the adaptors 45, urging the adaptors 45 outwards and therefore urging the radial interfaces 31 into the openings of the casing 15.

Figure 4I:
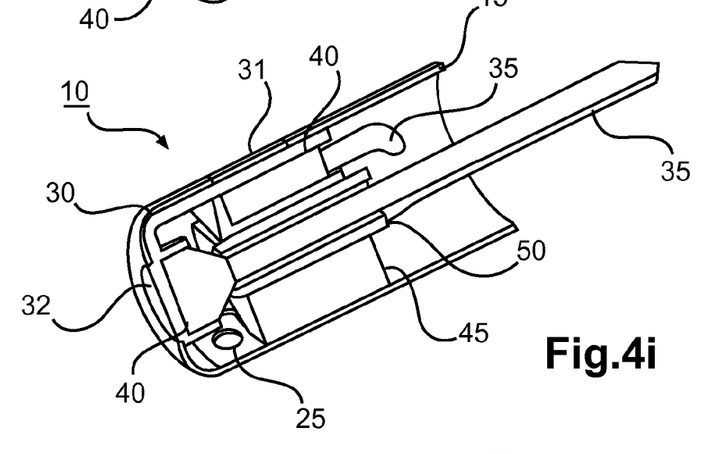

FIG. 4i shows a further step in the assembling of the ablation catheter tip following the state of FIG. 4h. Following the state of the assembling as illustrated in FIG. 4h, in FIG. 4i the fixing element 50 is completely inserted between the adaptors 45 and is now further in abutment with the front transducer 40, also fixing the front transducer 40 in position, with the axial interface 32 being fixed in the front opening 20 of the casing 15.

The outer surfaces of the radial interfaces 31 and the axial interface 32 are flush with the outer surface of the casing 15 (and the edges of the openings), wherein furthermore the combination of the surfaces of the interfaces 31, 32 and the casing 15 is smooth.

Figure 4J:
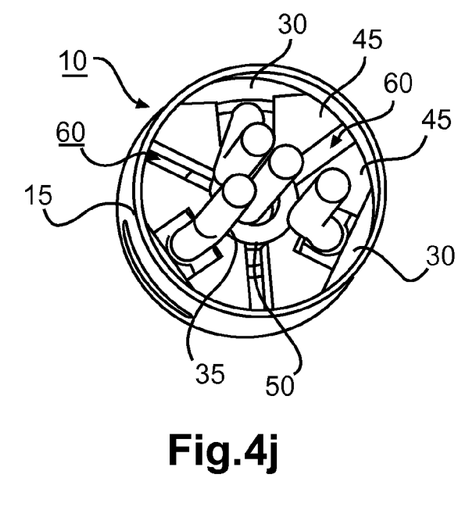
Figure 4K:
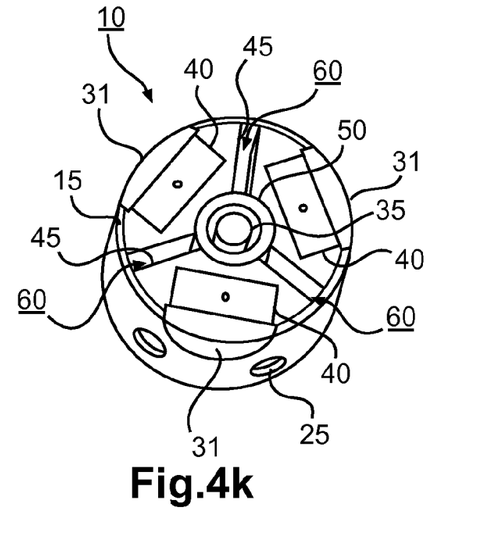

FIG. 4j and FIG. 4k show two cross sectional views of the state illustrated in FIG. 4i of the assembled ablation catheter tip. As indicated above, the outer surfaces of the radial interfaces 31 are flush with the outer surface of the casing 15. The adaptors 45 are urged outwards and separated from each other by the fixing element 50, such that the contact surfaces 49 of the adaptors 45 are separated from each other. Thus, by the inner surface of the casing 15, the contact surfaces 49 of the adaptors 45 and the outer surface of the fixing element 50, conduits 60 are formed, which are in fluid connection with the through-holes 25 of the casing 15.

Figure 5A:
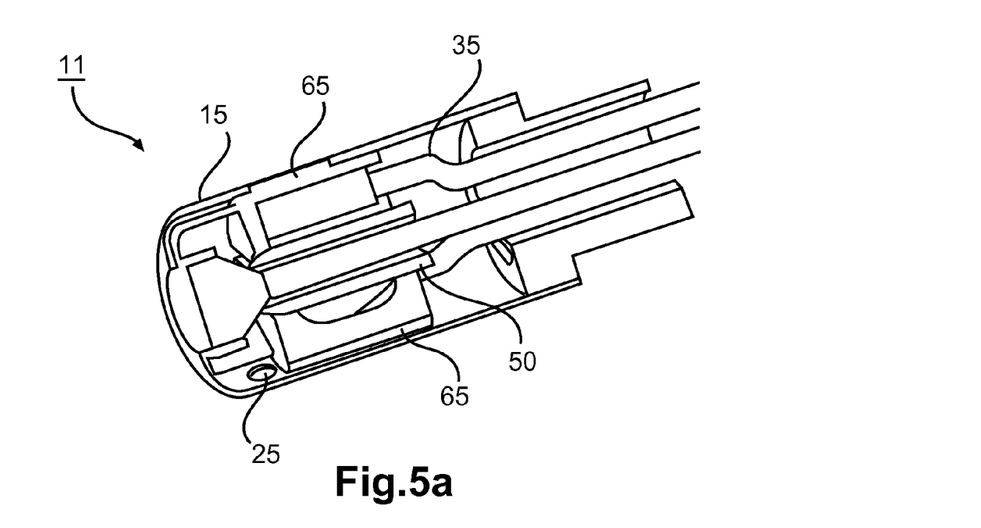
Figure 5B:
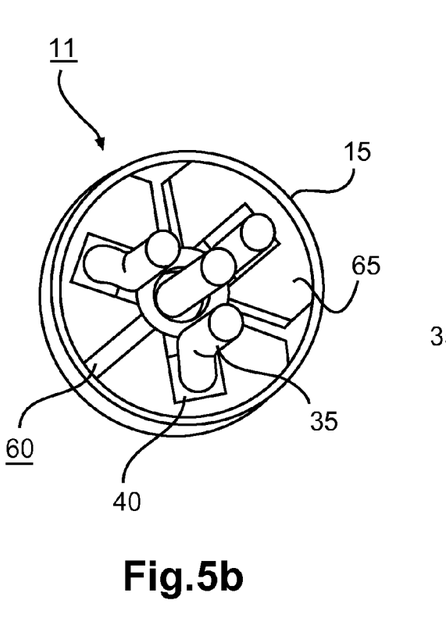
Figure 5C:
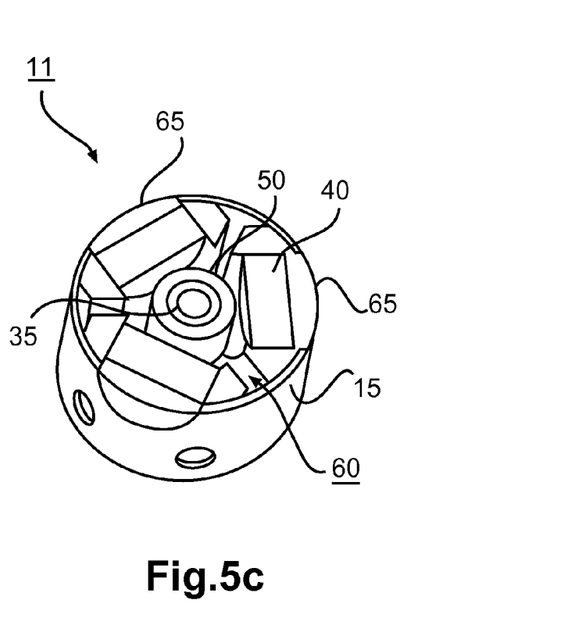

FIG. 5a to FIG. 5c show sectional views of an ablation catheter tip 11 in accordance with another embodiment of the invention. The ablation catheter tip 11 as another example of an interventional device according to the present invention differs from the ablation catheter tip 10 discussed above in that the separately provided signal interface 30 and the adaptors 45 are replaced by an integral combination 65, providing the functionality of the interface 30 and the adaptors 45. The combination 65 is provided with the transducers 40 in corresponding manner and also the other steps of the assembling discussed above are provided in a corresponding manner.

As it can be seen in particular in FIGS. 4i, 4j, 4k, 5a, 5b and 5c, as well as FIG. 2b, the signal assemblies which here include the signal interfaces 30, the transducers 40 and the adaptors 45 or the combinations 65 and the transducers 40, respectively, are locked in place between the casing 15 and the fixing element 50 such there is no danger of a portion of these elements "falling" out of the interventional device 10 during operation thereof.

Figure 6:
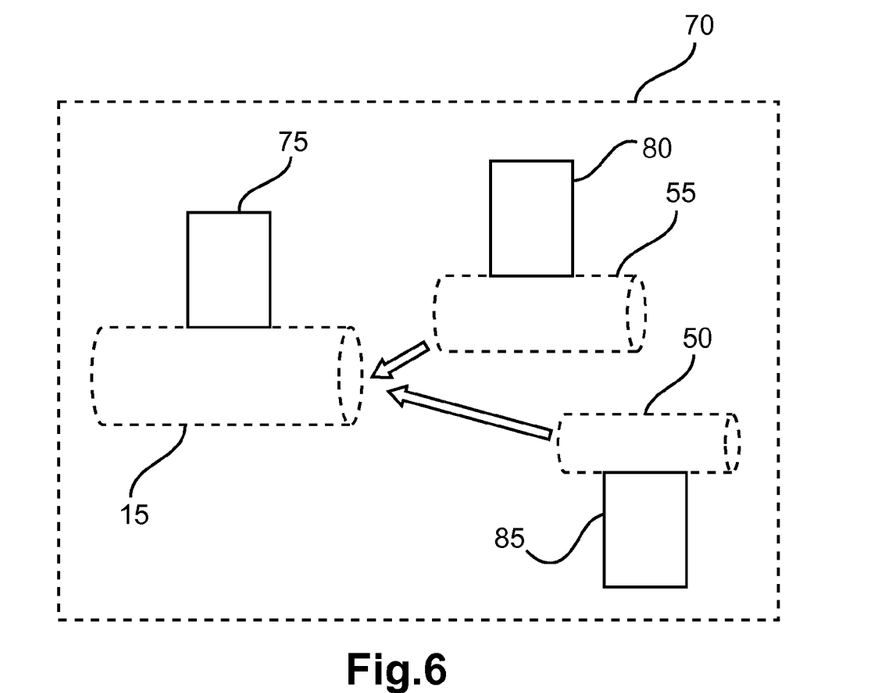
FIG. 6 shows an assembling system for an interventional device in accordance with a further embodiment of the invention.

FIG. 6 shows an assembling system 70 for an interventional device in accordance with a further embodiment of the invention. The assembling system 70 includes a holder 75, a first inserter 80 and a second inserter 85. The holder 75 is provided for holding a casing 15, wherein the first inserter is provided for the sub-assembly 55 (see above) with the second inserter 85 being provided for the fixing element 50 (see above). Once the sub-assembly 55 is inserted by the first inserter 80 in the casing 15 held by the holder 75, the second inserter 85 urges the fixing element into the casing, thereby urging the signal assemblies of the sub-assembly 55 into the respective openings of the casing 15 such that the outer surfaces of the signal assemblies and an outer surface of the casing are flush and edges of the opening and the outer surfaces of the signal assemblies and the outer surface of the casing form a smooth outer surface of the interventional device.

Figure 7:
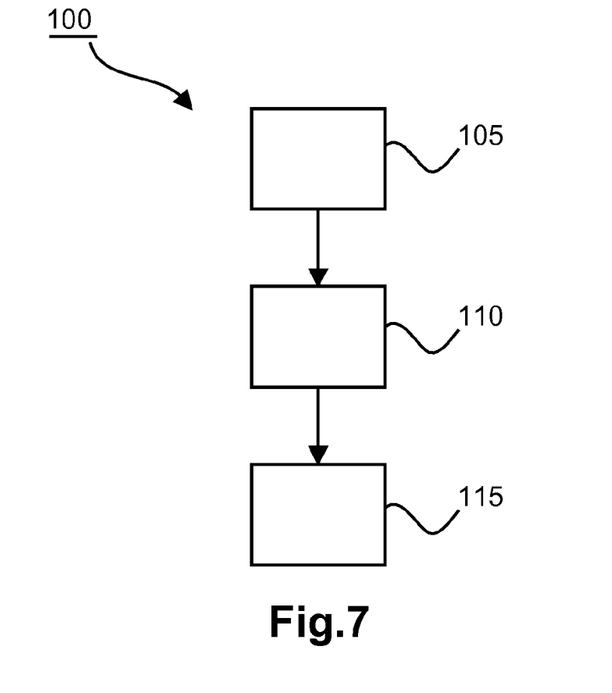
FIG. 7 shows a flow diagram illustrating a method of assembling an interventional device in accordance with yet a further embodiment of the invention.

FIG. 7 shows a flow diagram illustrating a method of assembling an interventional device in accordance with yet a further embodiment of the invention.

The method of assembling 100 includes the steps of providing a casing (step 105), inserting a plurality of signal assemblies into the casing (step 110) and urging the signal assemblies into respective openings (step 115). The casing is provided with a side wall having a plurality of openings extending in a direction oblique of openings extending in a direction oblique to a longitudinal axis of the casing (see FIG. 3e). Upon inserting (step 110) the plurality of signal assemblies into the casing, each signal assembly is aligned with one of the openings of the casing, wherein each signal assembly includes a sensor for receiving and/or an emitter for emitting signals through said opening. The urging (step 115) is provided by inserting a fixing element into the casing, such that the inserted fixing element fixes the signal assemblies and the respective openings from inside the casing (see FIGS. 4h, 4i and 5a).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

Even though the fixing element is illustrated herein as being one piece or integral, the present invention allows also for the fixing element comprising sub-elements, which might, for example, also interact with each other or with the other portions of the interventional device before, upon and/or after inserting the fixing element.

The shape of the openings is illustrated as being basically circular in the illustrated embodiments, while also other shapes are possible. The openings are further illustrated as corresponding to a boring (i.e. having basically constant cross-sections from the inside the casing to the outside of the casings). Nevertheless, the present invention is not limited to such form and the opening may, for example, also be (partially) tapering and/or may include a chamfer on the inside of the casing.

Additional sensors such as one or more thermocouples, optical fibers, etc. can be easily integrated in the interventional device making use of the space provided with the assembling technique when elements are locked into position (the fixing element may be hollow, there is available space between the sensor assemblies, etc.).

The above illustrative embodiments focus on the case of an ablation catheter tip, whereas the invention is limited neither to this particular field nor to the example of a catheter as an interventional device. An interventional needle or other interventional catheters, for example, may also be provided according to the present invention.

The number of signal assemblies is four in the illustrated embodiments (one front signal assembly and three signal assemblies directed outwards), while the present invention is not limited to such number and to such directions. Each individual senor may represent an array of sensors.

The present invention is not limited to ultrasound transducers as examples of the signal assemblies as also other sensors and emitters are possible and combinable (e.g. measuring an electric or magnetic signal, a temperature, a pH-value, etc.)

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like the control of steps for the assembling system can be implemented as program code means of a computer program and/or as dedicated hardware.

A computer program or software product may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An interventional device, comprising:
   a casing with a cylindrical-shaped side wall having a plurality of openings extending in directions oblique to a longitudinal axis of the casing;
   a sub-assembly including a signal interface and a plurality of signal assemblies, each signal assembly including a sensor and/or an emitter;
   a fixing element adapted to fix the plurality of signal assemblies within the casing from inside the casing via mechanically locking each signal assembly of the plurality of signal assemblies between the casing and the fixing element, wherein each signal assembly is aligned with a respective opening of the plurality of openings in the casing for receiving and/or emitting signals through the respective opening, wherein the fixing element urges adjacent abutting ones of the plurality of signal assemblies radially outward and physically separate from each other, and wherein the signal interface extends from the inside of the casing into the plurality of openings such that (i) an outer surface of the signal interface and an outer surface of the casing are flush at an edge of each respective opening of the plurality of openings, and (ii) the outer surface of the signal interface and the outer surface of the casing form a continuous outer surface of the interventional device; and
   one or more conduits extending within the casing, wherein the one or more conduits each comprise a conduit that is formed only by, and in response to, all of (i) the casing, (ii) adjacent signal assemblies of the plurality of signal assemblies and (iii) the fixing element being in an assembled state of the interventional device.

2. The interventional device according to claim 1, wherein the signal assemblies are positively locked, respectively, between the casing and the fixing element and/or to the fixing element.

3. The interventional device according to claim 1, wherein the casing further includes one or more through-holes in fluid connection to the one or more conduits.

4. The interventional device according to claim 1, wherein the outer surface of the signal assembly is at least partially a surface of the signal interface.

5. The interventional device according to claim 1, wherein at least a part of said outer surface of each signal assembly of the plurality of signal assemblies is a surface of the sensor and/or emitter of the respective signal assembly.

6. The interventional device according to claim 1, wherein a signal assembly includes an adaptor provided between the sensor and/or emitter of the signal assembly and the fixing element.

7. The interventional device according to claim 1,
   wherein the casing further includes a dome-shaped front-end wall, wherein the dome-shaped front-end wall is provided with an opening,
   wherein the sub-assembly further includes a further signal assembly provided with an emitter for emitting and/or a sensor for receiving signals through the opening in the dome-shaped front-end wall, the signal interface extending from the inside of the casing into the opening in the dome-shaped front-end wall such that (i) an outer surface of the signal interface and an outer surface of the front casing are flush at an edge of the opening in the dome-shaped front-end wall, and (ii) the outer surface of the signal interface and the outer surface of the casing form a continuous outer surface of the interventional device, absent discontinuities in the outer surface.

* * * * *